(12) United States Patent
Khreibani

(10) Patent No.: US 12,227,505 B2
(45) Date of Patent: Feb. 18, 2025

(54) SUPERCRITICAL FLUID EXTRACTION PROCESS WITH INTEGRATED PRESSURE EXCHANGER

(71) Applicant: James Khreibani, Miami Beach, FL (US)

(72) Inventor: James Khreibani, Miami Beach, FL (US)

( * ) Notice: Subject to any disclaimer, the term of this patent is extended or adjusted under 35 U.S.C. 154(b) by 444 days.

(21) Appl. No.: 17/592,449

(22) Filed: Feb. 3, 2022

(65) Prior Publication Data

US 2022/0242864 A1    Aug. 4, 2022

Related U.S. Application Data

(60) Provisional application No. 63/145,044, filed on Feb. 3, 2021.

(51) Int. Cl.
*C07D 473/12*    (2006.01)
*B01D 11/02*    (2006.01)

(52) U.S. Cl.
CPC ........ *C07D 473/12* (2013.01); *B01D 11/0203* (2013.01); *B01D 11/0257* (2013.01); *B01D 11/0284* (2013.01)

(58) Field of Classification Search
CPC .............. C07D 473/12; B01D 11/0203; B01D 11/0257; B01D 11/0284
See application file for complete search history.

(56) References Cited

U.S. PATENT DOCUMENTS

| | | | | |
|---|---|---|---|---|
| 4,820,537 A | * | 4/1989 | Katz ....................... | A23F 5/206 426/433 |
| 4,996,317 A | * | 2/1991 | O'Brien .................. | A23F 5/206 210/511 |
| 5,338,575 A | * | 8/1994 | Ben-Nasr ................ | A23F 5/208 426/427 |

* cited by examiner

*Primary Examiner* — Sikarl A Witherspoon

(57) ABSTRACT

Processes and apparatuses for soluble compound recovery using supercritical fluid (SCF) are disclosed. An example process involves solvent extraction of a soluble compound using a SCF from a solid or liquid substrate including, but not limited to, microalgae, plant matter, and polymers. The apparatus comprises SCF, an extraction vessel, a pressure exchanger, a separate soluble compound, and solid or liquid compound separators.

22 Claims, 9 Drawing Sheets

SUPERCRITICAL FLUID EXTRACTION PROCESS WITH INTEGRATED PRESSURE EXCHANGER

CROSS-REFERENCE TO RELATED APPLICATIONS

This non-provisional patent application claims priority to provisional patent application Ser. No. 63/145,044, filed 3 Feb. 2021, the contents of which are incorporated herein by reference

FIELD OF THE INVENTION

The present invention relates to a process and apparatus for supercritical (SCF) extraction using pressure differentials and an integrated pressure exchanger.

BACKGROUND OF THE INVENTION

The following is a tabulation of related art that presently appears relevant:

| U.S. Patents | | | |
|---|---|---|---|
| Patent No. | Kind Code | Issue Date | Patentee |
| 4,996,317 | A | 1991 Feb. 26 | O'Brien et al |
| 4,820,537 | A | 1989 Apr. 11 | Katz |

| Foreign Patent Documents | | | | |
|---|---|---|---|---|
| Patent Number | Country Code | Kind Code | Issue Date | Patentee |
| 0,941,140 | EP | B1 | 1999 Sep. 15 | Kanel |

| Non-patent Literature Documents | | |
|---|---|---|
| Title | Issue Date | Author |
| Recent advances in scaling-up of non-conventional extraction techniques: Learning from successes and failures | 2020 Apr. 14 | Belwal |
| Approach to biodiesel production from microalgae under supercritical conditions by the PRISMA method | 2019 August | Ortiz-Martinez |

Solvent extraction is a method to separate compounds based on their relative solubilities. In typical supercritical fluid extraction processes, the SCF is heated and pressurized sufficiently to transform the substance into its supercritical phase where it is contacted with a solid or liquid substrate in order to extract the soluble compound from within the solid or liquid substrate. In the extraction processes, it is generally desirable to reuse the SCF. Thus, it is desirable to remove the soluble compound and the insoluble solid or liquid compound from the recycled SCF. In the case of microalgae, rapeseed, and other particulate forms of solid or liquid substrate, there is no commercial method for removing both the soluble compound and the spent insoluble solid from the SCF while maintaining high pressure or supercritical conditions in a closed-loop extraction process. Known methods in the art involve cooling the reactor, depressurizing the reactor, or use additional absorption fluid[,] or replenish solid or liquid substrate feedstock in batches. Such additional processing steps in conventional methods of SCF extraction result in an increased cycle time, excess energy consumption, and fatigue stress on the mechanical structure. It is known in the art that the use of a pressure exchanger, also known as an energy recovery device, is used in commercial desalination plants to transfer the energy from a high-pressure brine discharge into a low-pressure seawater intake similar to a turbocharger. Pressure exchangers are also commonly used as they make the process more cost-effective. However, common methods of supercritical fluid extraction do not use pressure exchangers.

An example of industrial-scale supercritical fluid extraction process using a water scrubber is disclosed in U.S. Pat. No. 4,996,317 (O'Brian) entitled "Caffeine Recovery from Supercritical Carbon Dioxide". The process disclosed in O'Brian involves loading an extraction vessel also known as a reactor with coffee beans from a bean feeder. Once loaded, the extraction vessel is brought into contact with supercritical $CO_2$ which extracts the caffeine from the bean. The caffeine supercritical $CO_2$ solution then travels through a pipe to a water column where it is then sprayed with a countercurrent flow of water. The water absorbs the caffeine from the supercritical $CO_2$, allowing substantially pure $CO_2$ to leave the top of the water column for reuse. This disclosure's use of water within a carbon dioxide system is preferably used with a water-soluble solute and may, in some cases, result in undesirable carbonic acid corrosion, particularly when in addition to that naturally found within the coffee bean. The introduction of additional water into the process, may in some cases, reduce overall performance when used with certain solid or liquid substrates instead of coffee beans.

U.S. Pat. No. 4,820,537 (Katz) describes a method of periodically discharging used coffee beans from the bottom of an extraction vessel while un-decaffeinated beans are simultaneously replenished from a blow case pressure vessel into the top of the extraction vessel. The remainder of the disclosure generally follows the process described in U.S. Pat. No. 4,996,317. To isolate the high pressure within the extraction vessel from the blow case, a $CO_2$ isolation valve is closed and an atmospheric valve is opened to allow beans to enter the blow case chamber. To discharge the beans, the atmospheric valve is closed and the supercritical-$CO_2$ valve is opened, resulting in beans falling into the extraction vessel due to gravity. In addition to water-related issues, the use of a blow case as disclosed by Katz is not feasible for use with small particles such as microalgae due to their slow settling velocity. For example, and without limitation, according to Stokes Law, a 10-millimeter diameter-soaked spherical coffee particle has an approximate settling velocity of 0.2 m/s in 100 barG supercritical $CO_2$, whereas a dried spherical microalgae particle measuring a diameter of 50 microns has an approximate settling velocity of $7 \times 10^{-6}$ m/s. The significant increase in blow case clearance time for small particles when compared to coffee beans limits the practical use of the process described in Katz, particularly with respect to SCF extraction of small particles of biomass. Additionally, the process described in Katz may result in a portion of the fine biomass particles or liquid fractions to stay in the blow case and begin to form sediment around the valve contact faces, preventing proper isolation and resulting in extensive maintenance.

EP0941140 (Kanel) discloses a method of extracting a solute in the form of slurry within an extraction vessel of a specified size and operated inside a specific pressure and temperature range. The slurry described by Kanel is a combination of feedstock, solute, and carrier fluid. Among the deficiencies of Kanel includes, the introduction of water and other impurities, which can have a negative impact on supercritical fluid extraction as detailed by Ortiz-Martinez within "Approach to biodiesel production from microalgae under supercritical conditions by the PRISMA method".

As further detailed by Belwal in "Recent advances in scaling-up of non-conventional extraction techniques: Learning from successes and failures", there exists a need in the prior art for a process and apparatus for extracting a solute using a SCF in a manner that eliminates the need to depressurize the process to extract spent insoluble compound and replenish the SCF. In addition, there is a need for a method and apparatus for high-efficiency solute removal from SCFs which is cost-efficient, reduces or eliminates waste streams, and minimizes the duration of downtime for cleaning, repair, and maintenance.

SUMMARY OF THE INVENTION

The present invention relates to a apparatus and processes for extracting a soluble compound from a solid or liquid substrate that may comprise multiple small particles. For example, and without limitation, the SCF extraction process disclosed herein may involve extracting one or more compounds from microalgae, hemp, canola, and soybeans using a solvent such as $CO_2$ or $CH_3OH$. The invention can also be used for the extraction of two immiscible liquids. An example of SCF extraction system of the present disclosure comprises an extraction vessel and first compound and second compound separation vessels all acting substantially continuously within the supercritical phase or close to the supercritical phase. The use of a co-solvent such as ethanol, for example and without limitation is also within the scope of this invention.

For example and without limitation, a substantially pure SCF stream, at a sufficient pressure and temperature to support extraction, fills the extraction vessel, first compound separation vessel, and second compound separation vessel, whereby supercritical conditions are achieved. The solid or liquid substrate is fed into the extraction vessel through a solid or liquid compound loading chamber that is mechanically coupled to the extraction vessel. Generally, the loading chamber has pressure isolation valves installed on both ends, preventing the high extraction vessel pressure from escaping during loading and chamber clearing operations. The pressure boundary allows the solid or liquid compounds to substantially continuously enter the extraction vessel without vessel depressurization. The chamber may be cleared from the solid or liquid substrate by thoroughly blowing/flushing the chamber with the SCF at a higher pressure to ensure that the solid or liquid substrate substantially exits the chamber and flows past any isolation valves in order to prevent future damage.

Over a period of time, the SCF extracts the soluble compound from the solid or liquid substrate. The soluble compound is then separated from the SCF by using one or a plurality of separation techniques, including, but not limited to, cyclones, centrifuges, screens, or filters.

The remaining SCF and spent insoluble solid or liquid compound are then generally separated using cyclones and centrifuges or other suitable means. The spent insoluble solid or liquid compound travels to the second compound separation vessel where any remaining SCF is separated from the insoluble solid or liquid compound The present invention supports the use of small solid particles and liquid substrate and limits the number of substances within the process, thus reducing process degradation, reducing the formation of acidic and corrosive substances, removing additional waste streams, and generally maintaining a supercritical pressure and temperature that reduces expensive and time-consuming pressure and temperature cycles. In certain circumstances the use of a co-solvent such as ethanol or methanol, for example, may be used to accelerate the extraction process and remains within the scope of this invention.

BRIEF DESCRIPTION OF THE DRAWINGS

The various embodiments of this disclosure will be better understood by referring to the following detailed description and the accompanying drawings which illustrate the disclosed configurations.

101 SCF stream
102 extraction vessel
103 first compound separation vessel
104 second compound separation vessel
105 solid or liquid substrate feed
106 extraction flow transport pipe
107 first compound separator
108 first compound separator discharge
109 first compound separator return discharge
110 SCF recycle pipe
111 first compound separation vessel pressure reduction vent
112 soluble compound
113 insoluble flow transport pipe
114 second compound separator
115 second compound separator return discharge
116 second compound separator discharge
117 second compound separation vessel pressure reduction vent
118 insoluble solid or liquid compound
119 solid or liquid substrate loading chamber structure
120 extractor isolation valve
121 solid or liquid substrate isolation valve
122 SCF pressurization/vent connection
123 pressurization/vent connection isolation valve
124 SCF flow
125 solid screen
126 solid filter
127 supercritical compression device

201 SCF stream
202 extraction vessel
203 first compound separation vessel
204 second compound separation vessel
205 solid or liquid substrate feed
206 extraction flow transport pipe
207 soluble compound compression device
208 first compound separator return discharge
209 SCF recycle pipe
210 soluble compound
211 insoluble flow transport pipe 212 second compound separator
213 second compound separator return discharge
214 second compound separator discharge
215 first compound separation vessels pressure reduction vent
216 insoluble solid or liquid compound
217 extraction vessel circulation pipe
218 solid screen
219 solid filter
220 first compound separator
221 first compound separator return discharge
222 first compound separator discharge
223 Supercritical compression device

301 SCF stream
302 extraction vessel
303 first compound separation vessel
304 second compound separation vessel
305 extraction flow discharge pipe
306 pressure exchanger
307 insoluble flow isolation valve
308 insoluble flow separation pipe
309 solid or liquid substrate feed
310 feed circulation valve
311 extraction vessel return flow pipe
312 soluble compound separation isolation valve
313 soluble compound separation pipe
314 first compound separator
315 first compound separator return discharge
316 first compound separator discharge
317 soluble compound discharge
318 first compound separation vessels pressure reduction vent
319 first compound separator recycle valve
320 second compound separator
321 second compound separator return discharge pipe
322 second compound separator discharge
323 insoluble solid or liquid compound discharge
324 second compound separation vessels pressure reduction vent
325 second compound separator recycle valve
326 cavitation system supply pipe
327 cavitation system return pipe
328 SCF compression device

Figure 1A:
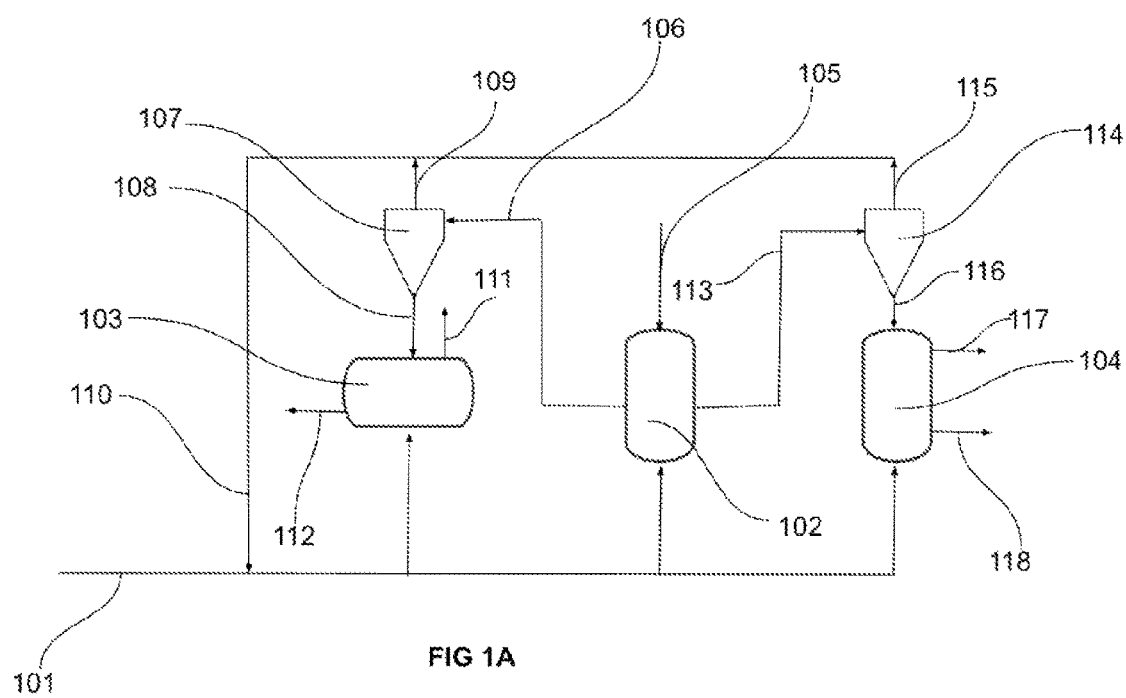
FIG. 1A to 1E show flow diagrams schematically illustrating the use of the SCF, pressure, and separators to produce a substantially pure soluble compound. The reference numerals represent the following.

401 SCF stream
402 extraction vessel
403 first compound separation vessel
404 second compound separation vessel
405 extraction flow discharge pipe
406 decompression device
406a mechanical shaft/electrical cable
406b compression device
407 insoluble flow isolation valve
408 insoluble flow separation pipe
409 solid or liquid substrate feed
410 feed circulation valve
411 extraction vessel return flow pipe
412 soluble compound separation isolation valve
413 soluble compound separation pipe
414 first compound separator
415 first compound separator return discharge
416 first compound separator discharge
417 soluble compound discharge
418 first compound separation vessels pressure reduction vent
419 first compound separator recycle valve
420 second compound separator
421 second compound separator return discharge pipe
422 second compound separator discharge
423 insoluble solid or liquid compound discharge
424 second compound separation vessels pressure reduction vent
425 second compound separator recycle valve
426 cavitation system supply pipe
427 cavitation system return pipe
428 SCF compression device

DETAILED DESCRIPTION OF THE INVENTION

Any substance above its critical temperature and pressure experiences a phase change into a SCF and exhibits properties between those of gases and liquids. Unlike gases, SCFs possess considerable solvent strength, and their transport properties are more favorable than liquid solvents due to their lower viscosity and increased diffusion coefficients. The density and solvent strength of the SCF may be modified over a modest range with small variations in temperature and pressure. This tunability may be used to control the behavior, separation process, extraction rates, and to specifically select which chemicals to extract.

The disclosure relates to apparatuses and processes for the extraction of a soluble compound from a solid or liquid insoluble compound when combined form a substrate generally, without limitation, comprising multiple small particles or droplets, respectively to accelerate extraction time. For example, and without limitation, techniques described herein may involve extracting soluble compounds from substrates such as canola, hemp, and microalgae using a SCF a solvent. For example, and without limitation, $CO_2$ may be used for SCF extraction due to its ability to perform SCF extraction at a relatively low pressure and temperature, and due to its abundance as a non-toxic natural substance. When for example and without limitation, a co-solvent such as ethanol is used to accelerate the extraction process is also within the scope of this invention.

More specifically, one embodiment of this disclosure is shown in FIG. 1A whereby a substantially pure SCF stream 101 or plurality of SCF streams 101 enters an extraction vessel 102, a first compound separation vessel 103, and a second compound separation vessel 104. The solid or liquid substrate feed 105 enters the extraction vessel 102 and makes contact with the SCF solvent, beginning the extraction process. After a period of time which is dependent on the specific SCF, the particular solid or liquid substrate used, and the process conditions, the soluble compound will be extracted from the solid or liquid substrate into the SCF solvent (not shown) leaving a substantially insoluble compound, that may be a solid or liquid (not shown).

The soluble compound, insoluble compound and SCF solvent mixture is conveyed as extraction flow from the extraction vessel 102, within the extraction flow transport pipe 106 to the first compound separator 107. The extraction flow transport pipe 106 is mechanically coupled to the extraction vessel 102 on the inlet and mechanically coupled to the first compound separator 107 on the outlet. The first compound separator 107, for example, and without limitation, a hydro-cyclone, centrifuge, coalescer, filter, another compound separator, or a combination thereof is known in the art and separates the soluble compound from the SCF and insoluble compound whereby the first compound separator discharge 108 enters the first compound separation vessels 103. The first compound separator return discharge 109 then leaves the first compound separator 107 and enters the SCF recycle pipe 110 where it may be reintroduced back into the process as part of the SCF stream 101 or other suitable connection between the recycle pipe 110 to the extraction vessel 102 (not shown). To support flow between the extraction vessel 102 and first compound separator 107, the first compound separation vessels pressure reduction vent 111 may be opened, creating high to low-pressure flow through the extraction flow transport pipe 106. The reduction in system pressure also reduces the density of the SCF, thus assisting the soluble compound to fall out of solution which, in turn, improves separation efficiency. The soluble compound 112 is then removed from the first compound separation vessel 103.

To remove the spent insoluble solid or liquid compound from the process, the spent insoluble solid or liquid compound and SCF are conveyed from the extraction vessel 102, within the insoluble flow transport pipe 113, to the second compound separator 114. The insoluble flow transport pipe 113 is mechanically coupled to the extraction vessel 102 on the inlet and mechanically coupled to the second compound separator 114 on the outlet. The second compound separator 114, for example, and without limitation, a hydro-cyclone, centrifuge, coalescer, filter, another compound separator, or combination thereof, is known in the art and separates the insoluble solid or liquid compound from the SCF whereby the second compound separator return discharge 115 comprising substantially SCF leaves the second compound separator 114 and enters the SCF recycle pipe 110 where it may be reintroduced back into the process as part of the SCF stream 101 or other suitable connection between the second compound separator return discharge 115 and extraction vessel 102 (not shown). The second compound separator discharge 116 enters the second compound separation vessel 104. To support flow between the extraction vessel 102 and the second compound separation vessel pressure reduction vent 117 may be opened, creating high to low-pressure flow through the insoluble flow transport pipe 113. The spent insoluble solid or liquid 118 is then removed from the second compound separator vessel 104.

Figure 1B:
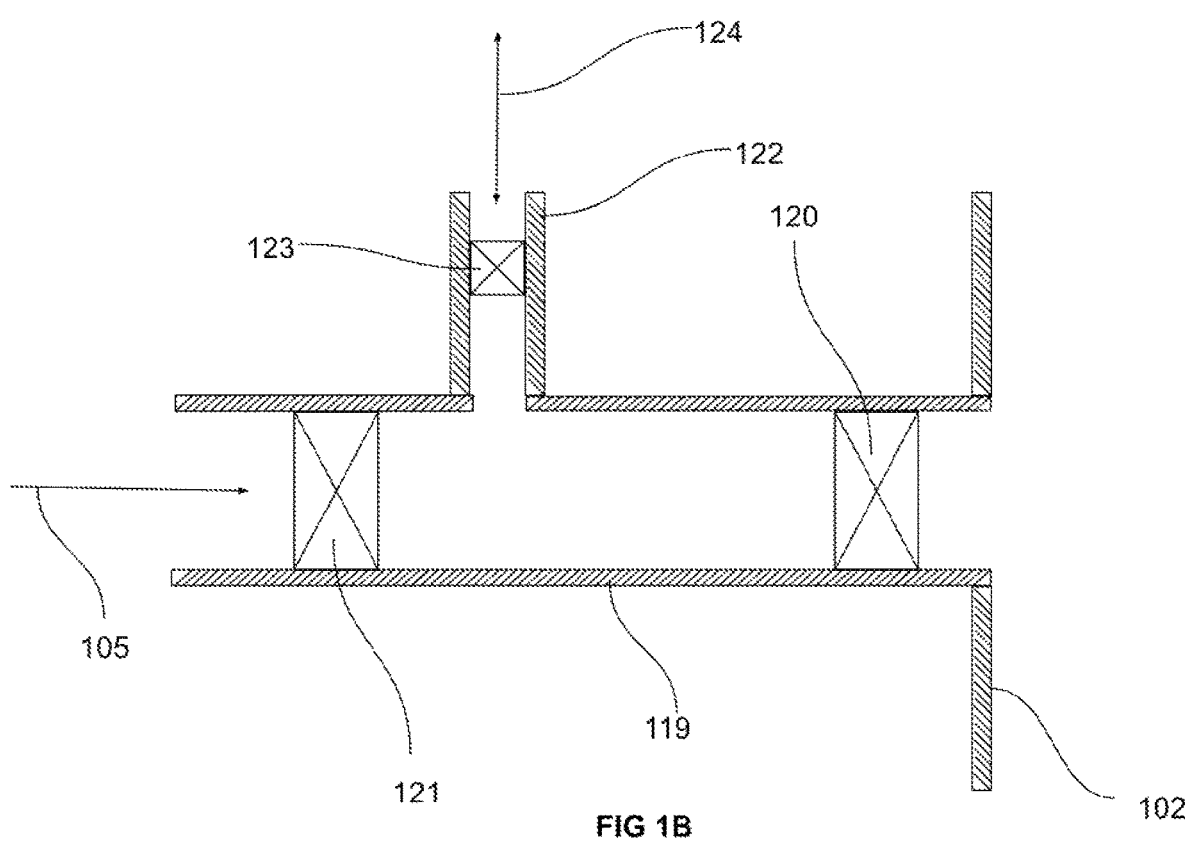

FIG. 1B discloses an example of a solid or liquid substrate loading mechanism that comprises a solid or liquid substrate loading chamber 119 mechanically coupled to the extraction vessel 102 structure. An extractor isolation valve 120 is mechanically coupled to the extraction vessel 102 and solid or liquid substrate loading chamber 119, preventing the release of pressurized SCF from the extraction vessel 102 during the loading of a solid or liquid substrate. A solid or liquid substrate Isolation valve 121 is mechanically coupled to the solid or liquid substrate loading chamber 119 and is opened to allow solid or liquid substrate feed 105 to enter the solid or liquid substrate loading chamber 119. When sufficient solid or liquid substrate feed 105 enters the solid or liquid substrate loading chamber 119, the solid or liquid substrate Isolation valve 121 is closed. Once the solid or liquid substrate Isolation valve 121 is closed, the extractor isolation valve 120 is opened to release the solid or liquid substrate feed 105 into the extraction vessel 102. It should be noted that interlocks (not shown) simultaneously prevent the opening of both the extractor isolation valve 120 and the solid or liquid substrate Isolation valve 121. To allow the solid or liquid substrate loading chamber 119 to depressurize trapped SCF between the extractor isolation valve 120 and solid or liquid substrate Isolation valve 121 prior to solid or liquid substrate loading a supercritical SCF pressurization/vent connection 122 is mechanically coupled to the loading chamber 119. A pressurization/vent connection isolation valve 123 is mechanically coupled to the supercritical SCF pressurization/vent connection 122 and when opened allows for the supercritical SCF flow 124 to be vented from the loading chamber 119. To remove the loaded solid or liquid substrate feed 105 from the loading chamber 119, the extractor isolation valve 120 and pressurization/vent connection isolation valve 123 is opened and pressurized SCF flow 124 pushes the solid or liquid substrate feed 105 into the extraction vessel 102 under pressure. In another embodiment of the same disclosure, ultrasonic probes (not shown) are installed to the solid or liquid substrate loading chamber structure 119 where they send ultrasonic waves (not shown) into the solid or liquid substrate as pretreatment to assist in the extraction process. FIG. 1B may be constructed as described or in other configurations, and connected to extraction vessel 102 or to other vessels (not shown) and pipework (not shown) and does not limit the scope of this invention.

Figure 1C:
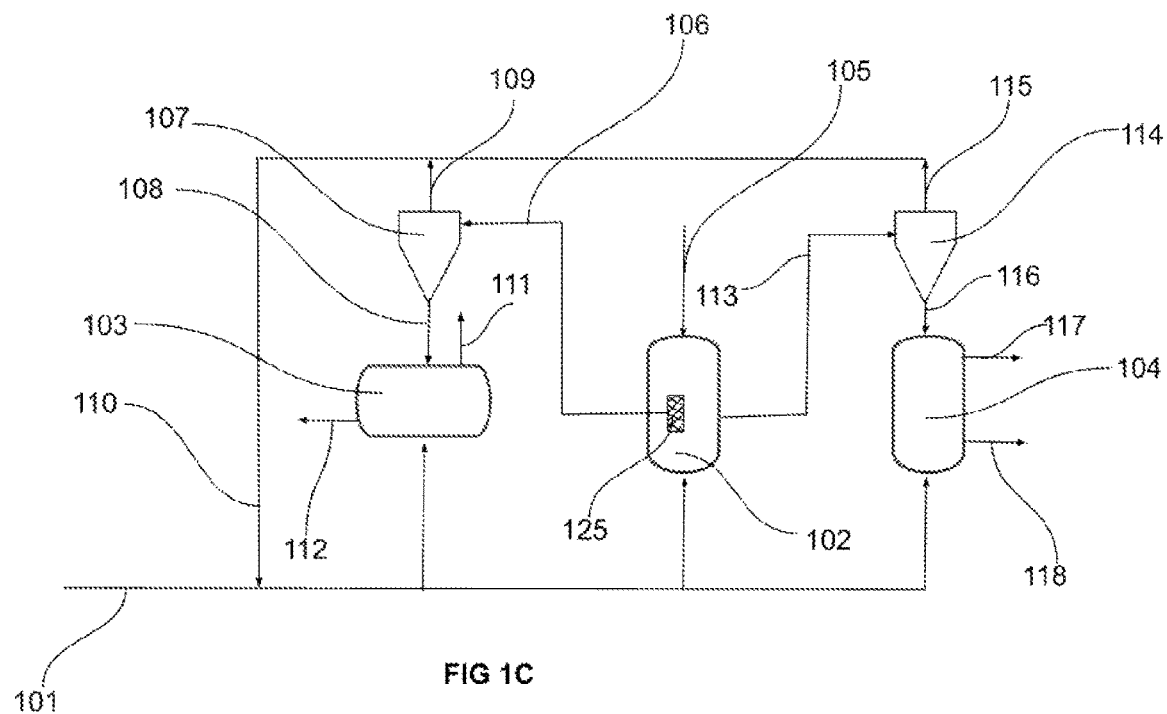

FIG. 1C discloses another embodiment of the same disclosure shown in FIG. 1A whereby a solid screen 125 is mechanically coupled to the inlet of the extraction flow transport pipe 106 to remove a portion of the solid or liquid substrate and/or insoluble solid or liquid compound before entering the first compound separator 107. For example, and without limitation, a solid screen may include a sieve or mesh, or other separation device mechanically coupled to the inlet of the extraction flow transport pipe 106, used for straining solids from at least one liquid, gas, and supercritical fluid.

Figure 1D:
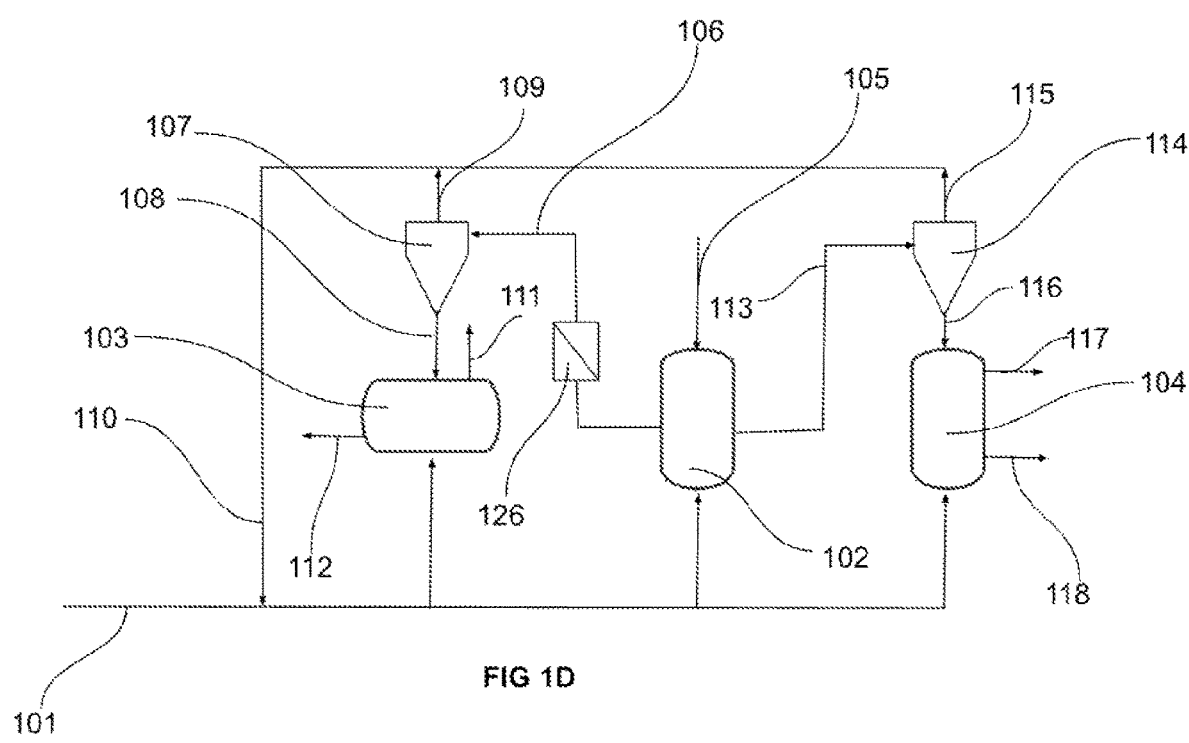

FIG. 1D describes another embodiment of the same disclosure shown in FIG. 1A whereby an additional solid filter 126, for example, and without limitation, a strainer, membrane, coalescer, or other and known in the art is mechanically coupled to the extraction flow transport pipe 106 between the extraction vessel 102 and the first compound separator 107.

Figure 1E:
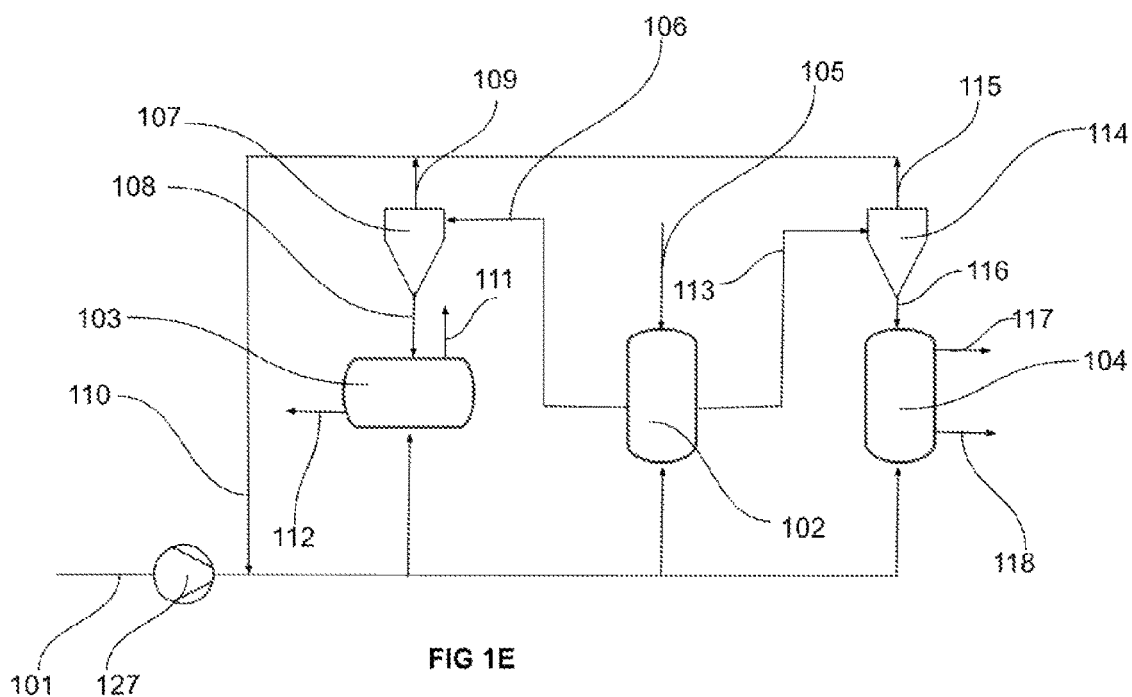

FIG. 1E describes another embodiment of the same disclosure shown in FIG. 1A whereby a supercritical compression device 127 is mechanically coupled to the supercritical SCF stream 101 upstream of the extraction vessel 102, a first compound separation vessel 103, and a second compound separation vessel 104. The supercritical compression device 127, which may include a compressor, a pump, an ejector, another compression device, or a combination thereof, provides sufficient pressure to turn the fluid supercritical. The subsequent steps described in FIG. 1A are repeated.

Figure 2A:
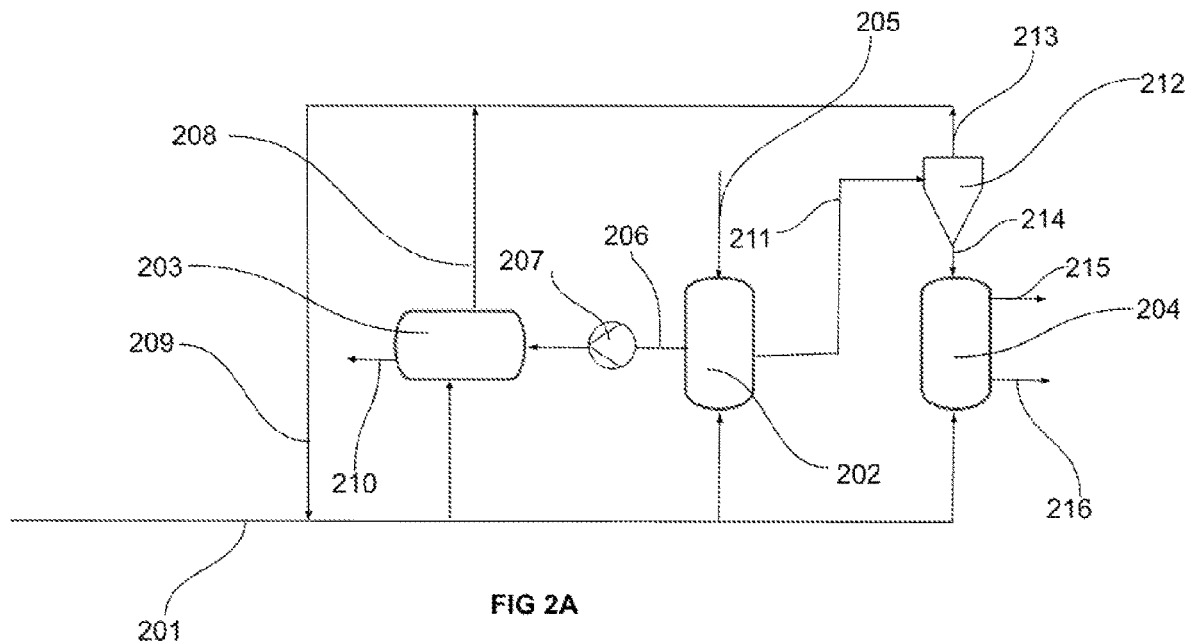
FIG. 2A to 2F show flow diagrams schematically illustrating the use of SCF, pressure, and separators to produce a separated soluble compound with the addition of compression devices to generate the conditions that enable SCF extraction. The reference numerals represent the following.

FIG. 2A describes another embodiment of the disclosure whereby a supercritical SCF stream 201 or plurality of SCF stream 201 enters an extraction vessel 202, a first compound separation vessel 203, and a second compound separation vessel 204. The solid or liquid substrate feed 205 enters the extraction vessel 202, following a similar method disclosed in FIG. 1B, and makes contact with the SCF solvent, beginning the extraction process. After a period of time that is dependent on the particular SCF, the solid or liquid substrate used, and the process conditions, the soluble compound solute will be extracted from the solid or liquid substrate into the SCF solvent.

The soluble compound, insoluble compound and SCF solvent mixture is conveyed as extraction flow from the extraction vessel extraction vessel 202, within the extraction flow transport pipe 206, to the soluble compound compression device 207, which may be, for example, and without limitation, a compressor, a pump, an ejector or another compression device. The soluble compound compression device 207 discharges into the first compound separation vessel 203, where the soluble compound separates from the SCF and insoluble compound separates from the solution and the first compound separator return discharge 208 leaves the first compound separation vessel 203 and enters the SCF recycle pipe 209 where it may be reintroduced back into the process as part of the SCF stream 201 or other suitable connection between first compound separation vessel 203 and extraction vessel 202 (not shown). The soluble compound 210 is then removed from the first compound separation vessel 203. The remainder of the process follows the steps described in FIG. 1A.

Figure 2B:
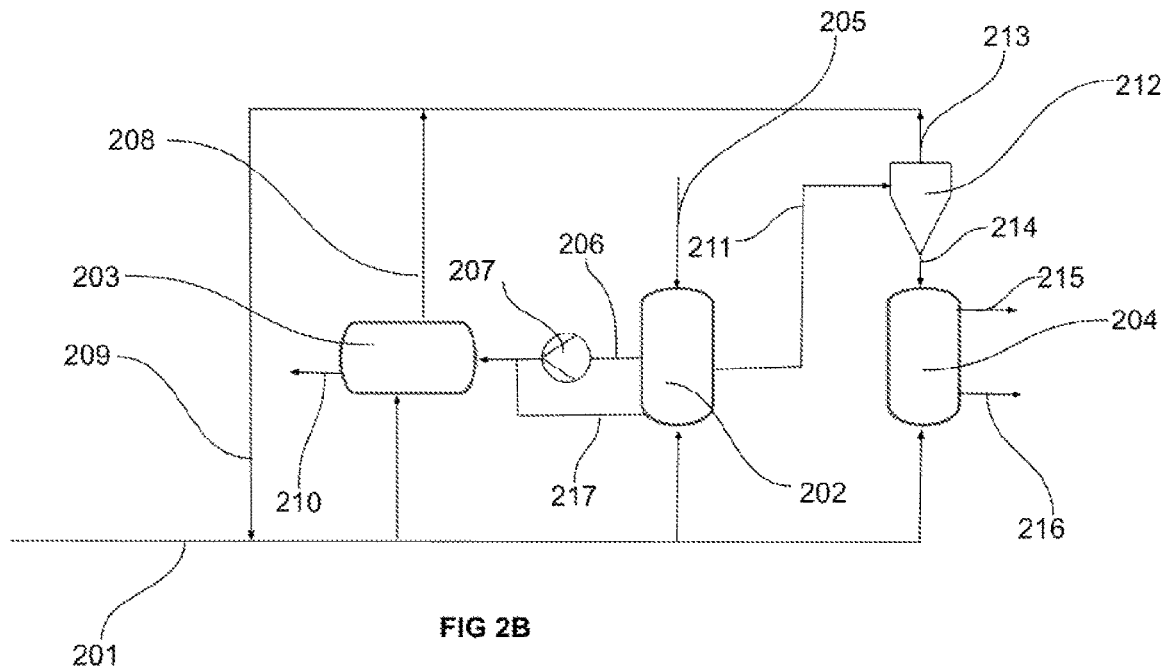

FIG. 2B describes another embodiment of the same disclosure shown in FIG. 2A whereby an extraction vessel circulation pipe 217 is mechanically coupled to the extraction flow transport pipe 206, downstream of the soluble compound compression device 207 and upstream of the first compound separation vessel 203. The extraction vessel circulation pipe 217 receives the soluble compound compression device 207 discharge and conveys the solution back into the extraction vessel 202. The circulated solution increases the rate of soluble compound extraction within the process. Once the extraction process is complete, the soluble compound compression device 207 begins discharging into the first compound separation vessel 203 where the subsequent steps described in FIG. 2A are repeated.

Figure 2C:
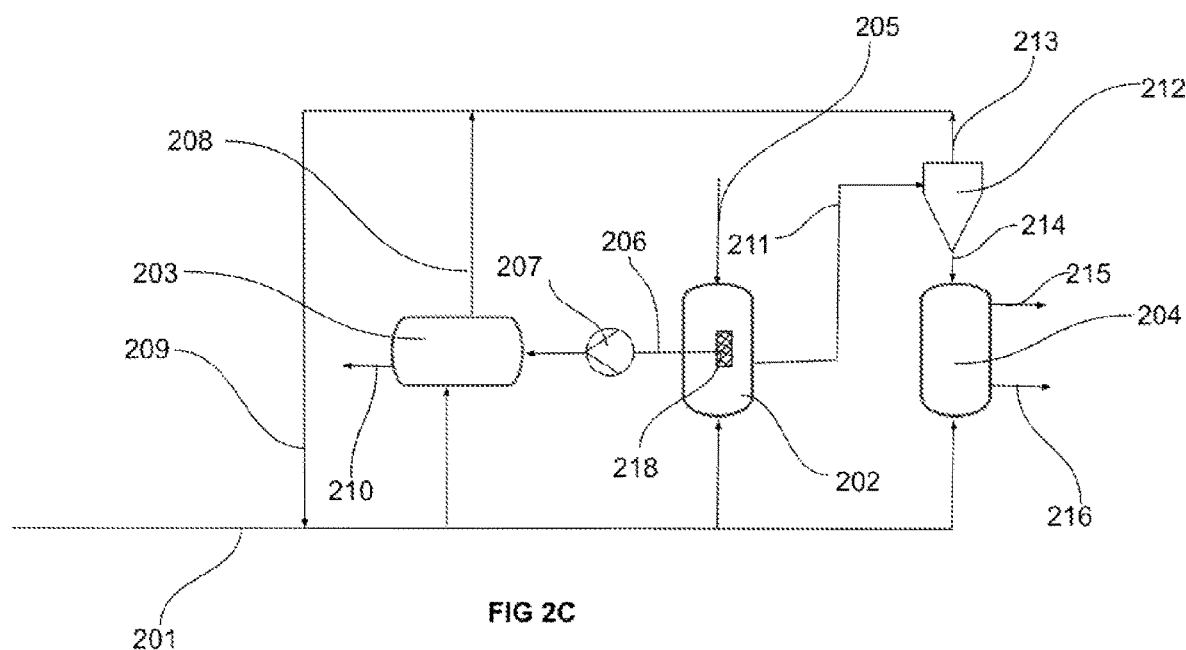

FIG. 2C describes another embodiment of the same disclosure shown in FIG. 2A whereby a solid screen 218 is mechanically coupled to the inlet of the extraction flow transport pipe 206 in order to remove a portion of solid or liquid substrate and/or insoluble solid or liquid compound before entering the first compound separator 203. The subsequent steps described in FIG. 2A are repeated.

Figure 2D:
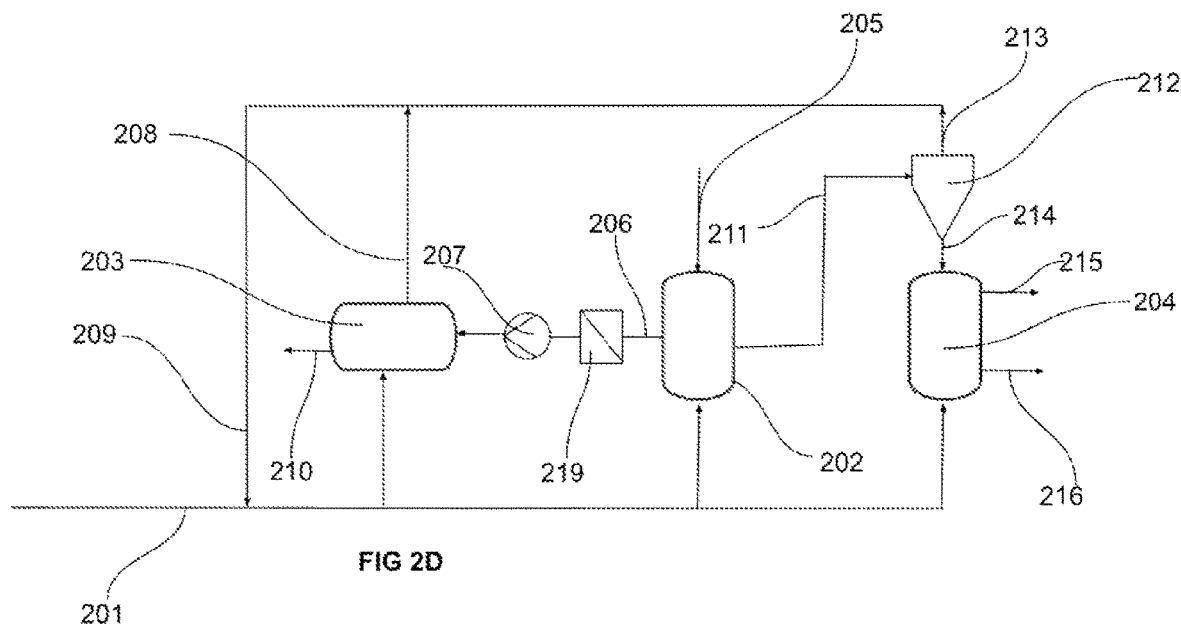

FIG. 2D describes another embodiment of the disclosure shown in FIG. 2A whereby an additional solid filter 219, for example, and without limitation, a strainer, membrane, coalescer, or another filter known in the art is mechanically coupled to the extraction flow transport pipe 206 between the extraction vessel 202 and the first compound separation vessel 203. The subsequent steps described in FIG. 2A are repeated.

Figure 2E:
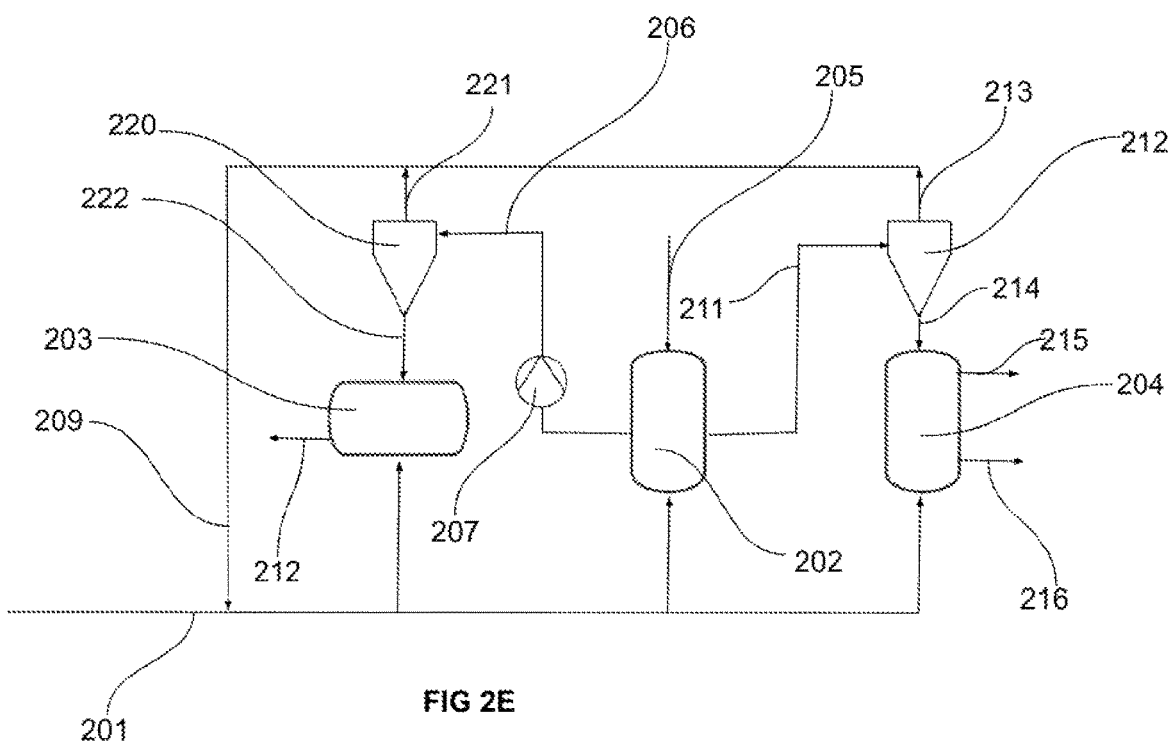

FIG. 2E describes another embodiment of the disclosure shown in FIG. 2A whereby the extraction flow transport pipe 206 is mechanically coupled to the extraction vessel 202 on the inlet and mechanically coupled to the first compound separator 220 on the outlet. The first compound separator 220, for example, and without limitation, may be a hydrocyclone, centrifuge, coalescer, filter, another compound separator known in the art, or a combination thereof. Said first compound separator 220 separates the soluble compound from the SCF whereby the first compound separator discharge 222 enters the first compound separation vessels 203. The first compound separator return discharge 221 leaves the first compound separator 220 and may enter the SCF recycle pipe 209 where it may be reintroduced back into the process as part of the SCF stream 201 or other suitable connection between first compound separator return discharge 221 and extraction vessel 202 (not shown). The subsequent steps described in FIG. 2A are repeated.

Figure 2F:
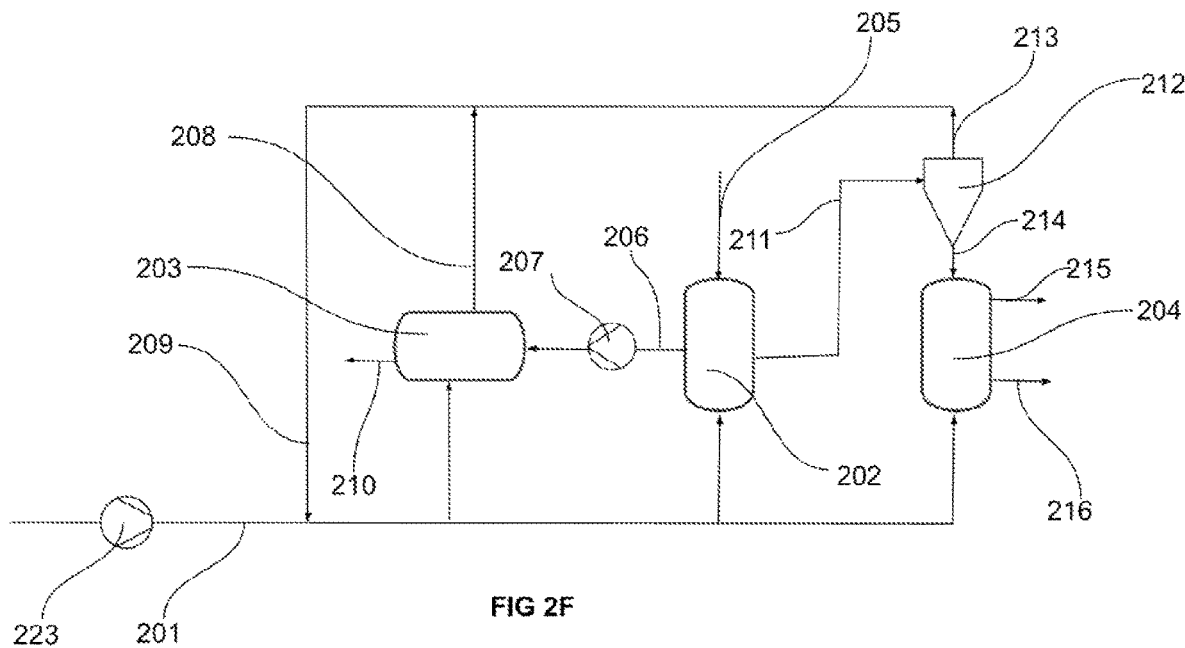

FIG. 2F describes another embodiment of the disclosure shown in FIG. 2A whereby a supercritical compression device 223, is mechanically coupled to the SCF stream 201 upstream of the extraction vessel 202, to a first compound separation vessel 203, and to a second compound separation vessel 204. The supercritical compression device 223, which may include a compressor, a pump, an ejector, another compression device known in the art, or a combination thereof, provides sufficient pressure to turn the fluid supercritical. The subsequent steps described in FIG. 2A are repeated.

Figure 3A:
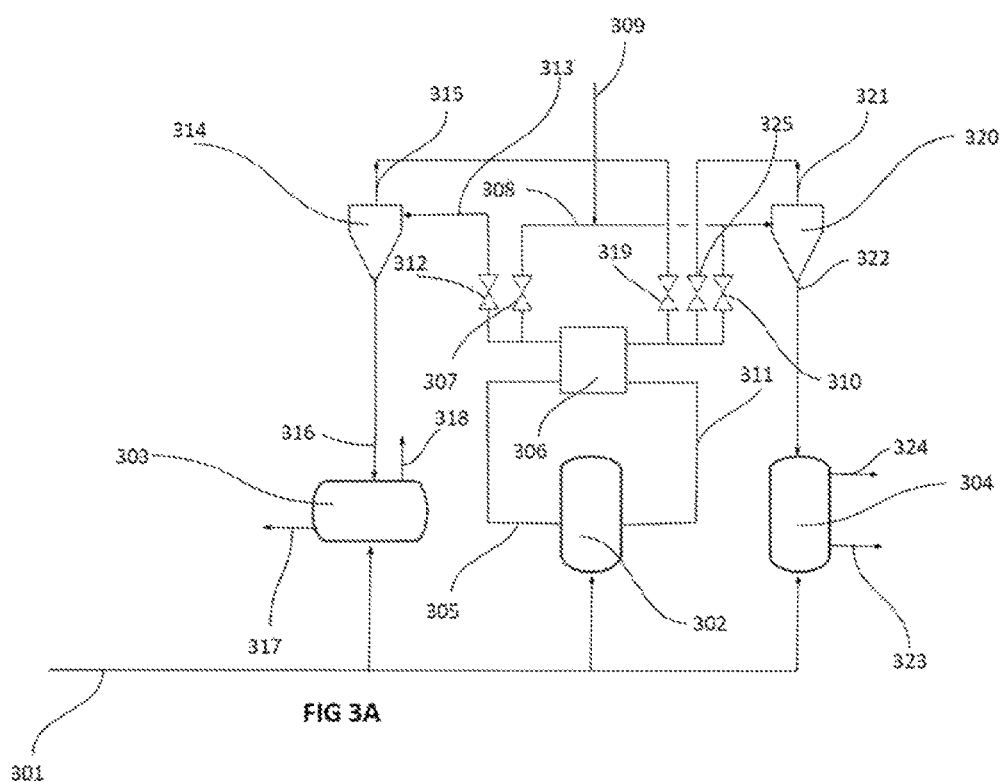
FIG. 3A to 3C show flow diagrams schematically illustrating the use of SCF, pressure, pressure exchanger, and separators to produce a separated soluble compound with the addition of compression devices to generate the conditions that enable SCF extraction. The reference numerals represent the following.

FIG. 3A describes another embodiment of the disclosure whereby a SCF stream 301 or plurality of SCF steams 301 is mechanically coupled to an extraction vessel 302, to a first compound separation vessel 303, and to a second compound separation vessel 304. The extraction vessels 302, first compound separation vessel 303, and second compound separation vessel 304 are filled with the content of the SCF stream 301 or plurality of SCF streams 301. Each separate vessel may operate at individually specified pressures. In one embodiment of the disclosure the SCF contained within the extraction vessel 302 is discharged from the extraction vessel 302 into the extraction flow discharge pipe 305. The extraction flow discharge pipe 305 is mechanically coupled to the extraction vessel 302 at the inlet and the pressure exchanger 306 at the outlet. The insoluble flow isolation valve 307 is mechanically coupled to the pressure exchanger 306 at the inlet and the insoluble flow separation pipe 308 at the outlet of the valve. When the insoluble flow isolation valve 307 is opened, flow conveys through the pressure exchanger 306 and is discharged at a lower pressure into the insoluble flow separation pipe 308.

The insoluble flow separation pipe 308 is mechanically coupled to the solid or liquid substrate feed 309 and may use the exemplary loading chamber principle detailed in FIG. 1B and may also be mechanically coupled to the other downstream pipework (not shown). The solid or liquid substrate feed 309 may also be mechanically coupled directly onto the extraction vessel 302 (not shown) as described in previous embodiments of the disclosure. In one embodiment of the disclosure described in FIG. 3A the solid or liquid substrate feed 309 is mechanically coupled to the insoluble flow separation pipe 308. There may be one or a plurality of discharges of the insoluble flow separation pipe 308, and one discharge is mechanically coupled to the feed circulation valve 310. The outlet of the feed circulation valve 310 is mechanically coupled to the pressure exchanger 306. When the feed circulation valve 310 is opened, flow is conveyed through the insoluble flow separation pipe 308 and discharged into the pressure exchanger 306. As the flow is conveyed through the pressure exchanger 306, the high pressure contained within the extraction flow discharge pipe 305 is transferred into the proportionately lower pressure flow within the insoluble flow separation pipe 308 using methods well known in the art. The pressure exchanger 306 discharges the flow into the extraction vessel return flow pipe 311 at increased pressure relative to that within the insoluble flow separation pipe 308. The extraction vessel return flow pipe 311 is mechanically coupled at one end to the pressure exchanger 306 and at the other end the extraction vessel 302, allowing flow to return to the extraction vessel 302.

Generally, when the density of the soluble compound exceeds the individual density of both the SCF and the insoluble solid or liquid compound, the soluble compound is removed from the process first and vice-versa when the density of the insoluble solid or liquid compound exceeds the density of the soluble compound and SCF. To separate the soluble compound from the insoluble solid or liquid compound and SCF substantially contained within the extraction vessel 302, the contents are discharged from the extraction vessel 302 and into the extraction flow discharge pipe 305. The extraction flow discharge pipe 305 is mechanically coupled to the extraction vessel 302 at the inlet and the pressure exchanger 306 at the outlet. The soluble compound separation isolation valve 312 is mechanically coupled to the pressure exchanger 306 at the inlet and the soluble compound separation pipe 313 at the discharge. When the soluble compound separation isolation valve 312 is opened, the flow is conveyed through the soluble compound separation pipe 313 to the first compound separator 314 as extraction flow. The first compound separator 314, for example, and without limitation, may comprise a hydrocyclone, a centrifuge, a coalescer, filter, another compound separator known in the art, or a combination thereof. The first compound separator 314 separates the soluble compound from the insoluble solid or liquid compound and SCF.

The first compound separator 314 removes the soluble compound from the SCF and insoluble compound and is mechanically coupled to the first compound separator return discharge pipe 315 and the first compound separator discharge 316. The substantially separated soluble compound is conveyed through the first compound separator discharge 316 into the mechanically coupled first compound separator vessel 303. The soluble compound can be stored in the first compound separator vessel 303 and/or removed from the process through the soluble compound separator discharge 317. In one embodiment of the disclosure the pressure may be regulated when if needed through the use of a first compound separator vessel pressure reduction vent 318 mechanically coupled to the first compound separator vessel 303. The flow substantially removed of the soluble compound leaving SCF and insoluble compound travels through the first compound separator return discharge pipe 315 that is mechanically coupled to the first compound separator recycle valve 319 or other valve allowing flow through the pressure exchanger 306. The discharge side of the first compound separator recycle valve 319 is mechanically coupled to the pressure exchanger 306 and when the first compound separator recycle valve 319 is opened, flow is discharged into the pressure exchanger 306. As the flow is conveyed through the pressure exchanger 306, the high pressure contained within the extraction flow discharge pipe 305 is transferred into the proportionately lower pressure flow within the first compound separator return discharge pipe 315. The discharge from the pressure exchanger 306 enters the extraction vessel return flow pipe 311 at increased pressure. The extraction vessel return flow pipe 311 is mechanically coupled to the pressure exchanger 306 and the extraction vessel 302 allowing for flow to return to the extraction vessel 302.

Generally, and dependent on relative densities, after the removal of the solute, the insoluble solid or liquid compound may be removed from the SCF substantially contained within the extraction vessel 302, where the contents are discharged from the extraction vessel 302 into the extraction flow discharge pipe 305. The extraction flow discharge pipe 305 is mechanically coupled to the extraction vessel 302 at the inlet and the pressure exchanger 306 at the outlet. The insoluble flow isolation valve 307 is mechanically coupled to the pressure exchanger 306 at the inlet and the insoluble flow separation pipe 308 at the discharge. When the solid or liquid separation isolation valve 307 is opened, the mixed insoluble solid or liquid compound and SCF exits the pressure exchanger 306 and is conveyed through the insoluble flow separation pipe 308. When the insoluble flow separation pipe 308 is also coupled to the feed circulation valve 310, the valve remains closed and the flow is discharged into the second compound separator 320 that is mechanically coupled to the insoluble flow separation pipe 308. The second compound separator 320, for example, and without limitation, may comprise a hydro-cyclone, centrifuge, coalescer, another compound separator known in the art, or combination thereof. Said compound separator separates the SCF from the insoluble solid or liquid compound. The second compound separator 320 separates the SCF from the insoluble solid or liquid compound and discharges the substantially pure SCF into the mechanically coupled second compound separator return discharge pipe 321 and the second compound separator 320 discharges the substantially pure second compound separator discharge 322 into the mechanically coupled Second compound separation vessel 304.

The insoluble solid or liquid compound may be stored in the second compound separation vessel 304 and/or removed from the process through the insoluble solid or liquid compound discharge 323 which is mechanically coupled to the second compound separation vessel 304. In one embodiment of the disclosure the pressure may be regulated if needed through the use of a second compound separation vessel pressure reduction vent 324 mechanically coupled to the second compound separation vessel 304. The substantially pure SCF with removed or reduced insoluble solid or liquid compound is conveyed from the second compound separator 320 through the second compound separator return discharge pipe 321 that is mechanically coupled to the second compound separator recycle valve 325. The discharge side of the second compound separator recycle valve 325 is mechanically coupled to the pressure exchanger 306. When the second compound separator recycle valve 325 is opened, flow is discharged into the pressure exchanger 306. As the flow is conveyed through the pressure exchanger 306, the high pressure contained within the extraction flow discharge pipe 305 is transferred into the proportionately lower pressure flow contained within the second compound separator return discharge pipe 321 using methods well known in the art. The discharge from the pressure exchanger 306 enters the extraction vessel return flow pipe 311 at increased pressure. The extraction vessel return flow pipe 311 is mechanically coupled to the pressure exchanger 306 and the extraction vessel 302, allowing flow to return to the extraction vessel 302.

Figure 3B:
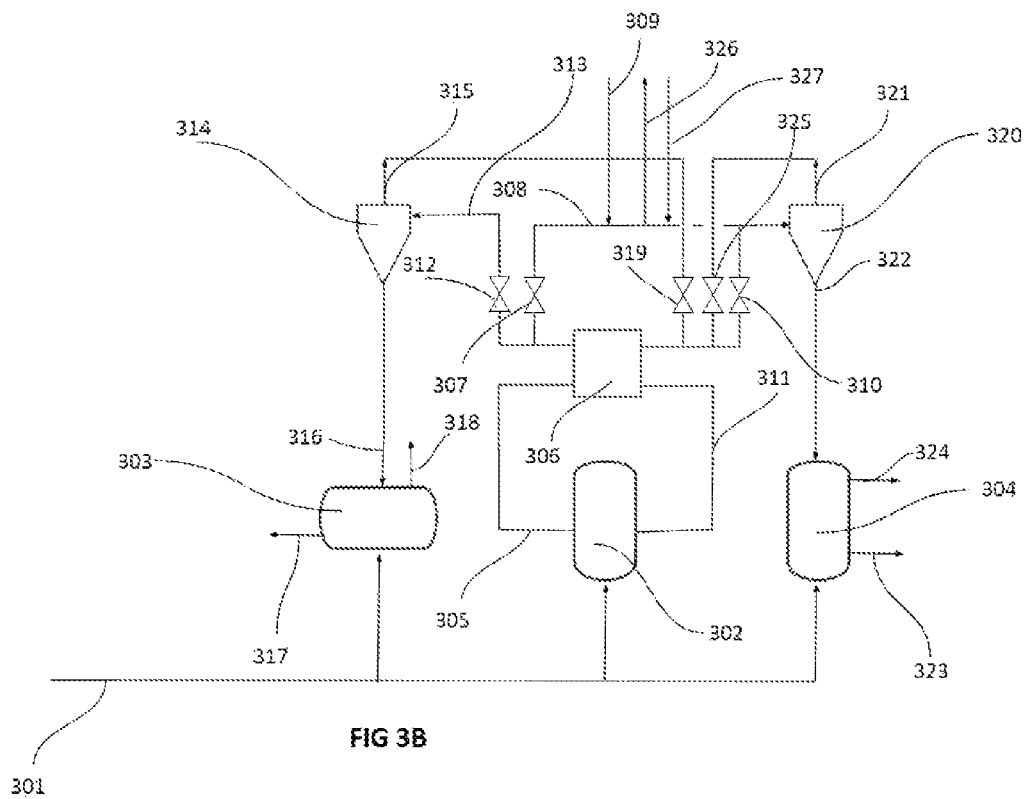

FIG. 3B describes another embodiment of the same disclosure whereby a cavitation system supply pipe 326 is mechanically coupled to the insoluble flow separation pipe 308 or other pipework or vessel (not shown). The flow substantially comprising SCF and a insoluble solid or liquid compound and/or solid or liquid substrate is conveyed through the cavitation system supply pipe 326 where it makes contact with a flow contraction (not shown). For example, and without limitation, the flow contraction (not shown) may be an orifice plate or venturi or other means that causes the pressure to be reduced in the flow below the SCF vapor pressure may be used. This reduction in pressure within the flow contraction (not shown) results in hydrodynamic cavitation that disrupts the solid or liquid substrate, thus increasing the rate of extraction. The flow is then discharged from the flow contraction (not shown) into a cavitation system return pipe 327 that is mechanically coupled to the flow contraction (not shown) and the insoluble flow separation pipe 308 or other pipework or vessel (not shown). The flow then discharges from the cavitation system return pipe 327 into the insoluble flow separation pipe 308 before being conveyed through the feed circulation valve 310. The subsequent steps described in previous embodiments are then followed. The cavitation system supply pipe 325 and cavitation system return pipe 326 may also be mechanically coupled to other sections of the system. For example, and without limitation, they may be coupled to the extraction vessel 302 or another vessel or pipe (not shown). Such embodiments utilizing interconnecting pipework (not shown) or vessels should be considered within the scope of this invention.

Figure 3C:
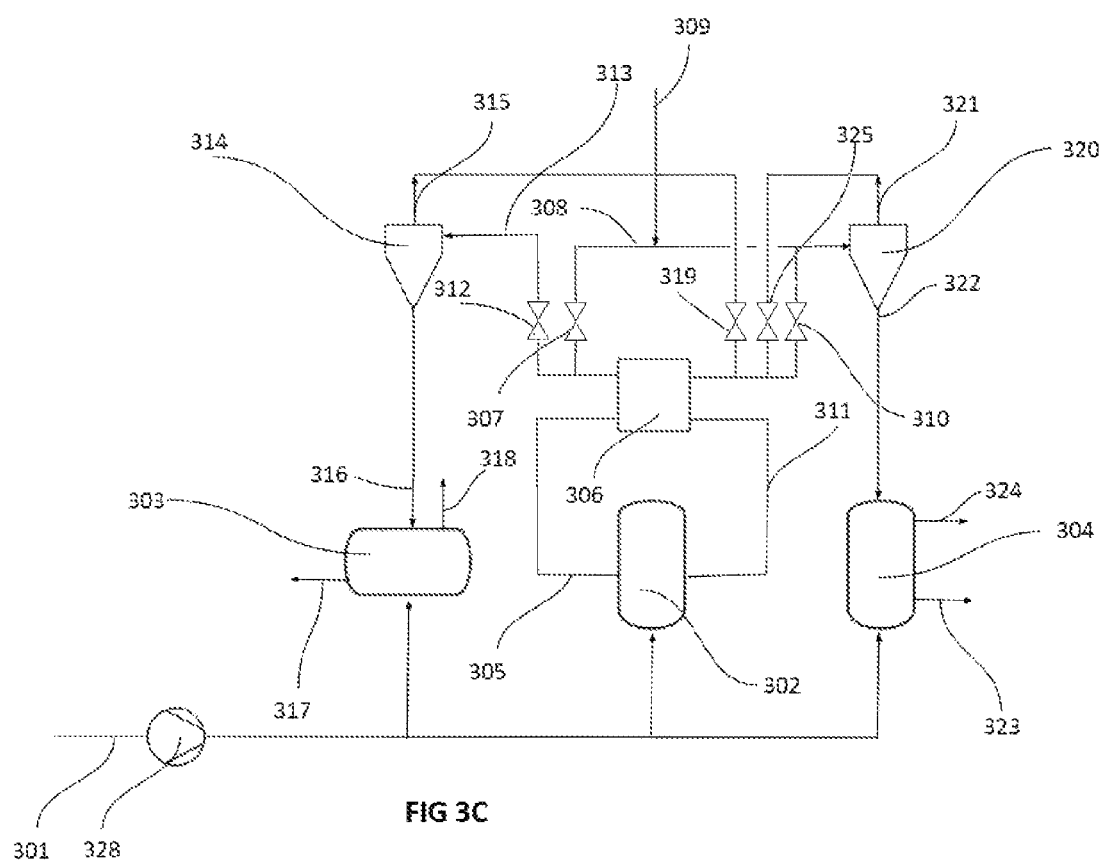

FIG. 3C describes another embodiment of the same disclosure where a SCF compression device 328 is mechanically coupled to the SCF stream 301 or plurality of SCF streams 301 at the inlet. The SCF compression device 328 discharge's into at least one of an extraction vessel 302, a first separation vessel 303, a second separation vessel 304, and other interconnecting pipework. The SCF compression device 328 allows for simultaneous or independent filling and pressurization of at least one of an extraction vessel 302, a first separation vessel 303, a second separation vessel 304, and other interconnecting pipework. The remainder of the steps within this embodiment of the same disclosure follow the steps described in previous embodiments.

Figure 4A:
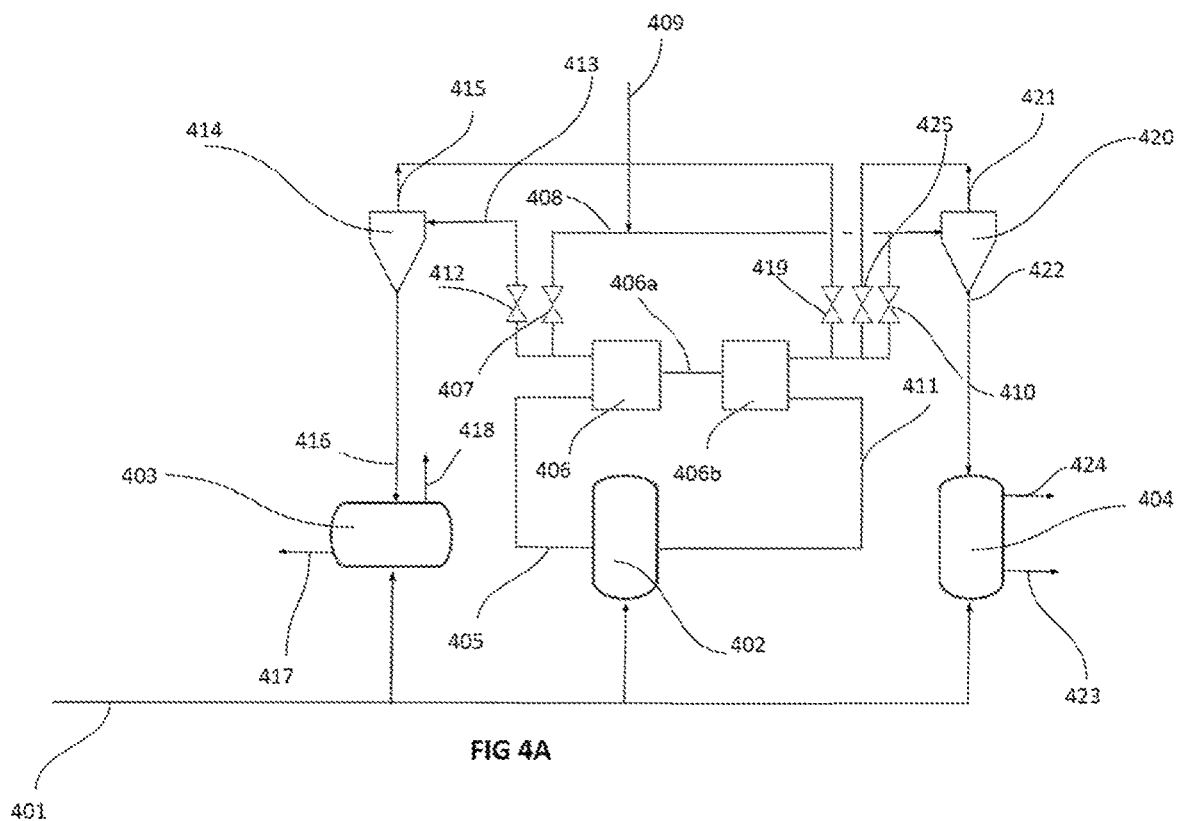
FIG. 4A to 4C show flow diagrams schematically illustrating the use of SCF, pressure, decompression device, compression device and separators to produce a separated soluble compound with the addition of compression devices to generate the conditions that enable SCF extraction. The reference numerals represent the following.

FIG. 4A describes another embodiment of the disclosure whereby a SCF stream 401 or plurality of SCF steams 401 is mechanically coupled to an extraction vessel 402, to a first compound separation vessel 403, and to a second compound separation vessel 404. The extraction vessels 402, first compound separation vessel 403, and second compound separation vessel 404 are filled with the content of the SCF stream 401 or plurality of SCF streams 401. Each separate vessel may operate at individually specified pressures. In one embodiment of the disclosure the SCF contained within the extraction vessel 402 is discharged from the extraction vessel 402 into the extraction flow discharge pipe 405. The extraction flow discharge pipe 405 is mechanically coupled to the extraction vessel 402 at the inlet and the decompression device 406 at the outlet. The decompression device 406 may for example and without limitation be a turbine or other device that takes a high pressure at the inlet and reduces the pressure at the outlet using methods known in the art. The energy that is lost across the decompression device 406 may be transferred for example and without limitation a mechanically coupled mechanical shaft/electrical cable 406a that is mechanically coupled at the other end to drive a compression device 406b. The insoluble flow isolation valve 407 is mechanically coupled to the decompression device 406 at the inlet and the insoluble flow separation pipe 408 at the outlet of the valve. When the insoluble flow isolation valve 407 is opened, flow conveys through the decompression device 406 and is discharged at a lower pressure into the insoluble flow separation pipe 408.

The insoluble flow separation pipe 408 is mechanically coupled to the solid or liquid substrate feed 409 and may use the exemplary loading chamber principle detailed in FIG. 1B and may be mechanically coupled directly onto the extraction vessel 402 (not shown) as described in previous embodiments of the same disclosure or onto the downstream pipework as shown in the current embodiment. In one embodiment of the disclosure described in FIG. 4A the solid or liquid substrate feed 409 is mechanically coupled to the insoluble flow separation pipe 408. There may be one or a plurality of discharges of the insoluble flow separation pipe 408, and one discharge is mechanically coupled to the feed circulation valve 410. The outlet of the feed circulation valve 410 is mechanically coupled to the compression device 406b which may include for example and without limitation a pump, compressor, a rotor or other means of compressing flow into a higher pressure then that received at the compression device 406b inlet. When the feed circulation valve 410 is opened, flow is conveyed through the insoluble flow separation pipe 408 and discharged into the compression device 406b. As the flow is conveyed through the compression device 406b, the high pressure energy contained within the extraction flow discharge pipe 405 is transferred into the proportionately lower pressure flow within the insoluble flow separation pipe 408 using methods well known in the art. The compression device 406b discharges the flow into the extraction vessel return flow pipe 411 at increased pressure relative to that within the insoluble flow separation pipe 408. The extraction vessel return flow pipe 411 is mechanically coupled at one end to the compression device 406b and at the other end the extraction vessel 402, allowing flow to return to the extraction vessel 402.

Generally, when the density of the soluble compound exceeds the individual density of both the SCF and the insoluble solid or liquid compound, the soluble compound is removed from the process first and vice-versa when the density of the insoluble solid or liquid compound exceeds the soluble compound and SCF. To separate the soluble compound from the solid or liquid compound and SCF substantially contained within the extraction vessel 402, the contents are discharged from the extraction vessel 402 and into the extraction flow discharge pipe 405. The extraction flow discharge pipe 405 is mechanically coupled to the extraction vessel 402 at the inlet and the decompression device 406 at the outlet. The soluble compound separation isolation valve 412 is mechanically coupled to the decompression device 406 at the inlet and the soluble compound separation pipe 413 at the discharge. When the soluble compound separation isolation valve 412 is opened, the flow is conveyed through the soluble compound separation pipe 413 to the first compound separator 414 as extraction flow. The first compound separator 414, for example, and without limitation, may comprise a hydro-cyclone, a centrifuge, a coalescer, filter, another compound separator known in the art, or a combination thereof. The first compound separator 414 separates the soluble compound from the insoluble solid or liquid compound and SCF.

The first compound separator 414 separates the soluble compound from the SCF and insoluble compound and is mechanically coupled to the first compound separator return discharge pipe 415 and the first compound separator discharge 416. The substantially separated soluble compound is conveyed through the first compound separator discharge 416 into the mechanically coupled first compound separator vessel 403. The soluble compound can be stored in the first compound separator vessel 403 and/or removed from the process through the soluble compound discharge 417. In one embodiment of the disclosure the pressure may be regulated when if needed through the use of a first compound separator vessel pressure reduction vent 418 mechanically coupled to the first compound separator vessel 403. The flow substantially removed of the soluble compound travels through the first compound separator return discharge pipe 415 diverting the SCF and insoluble compound to the mechanically coupled to the first compound separator recycle valve 419 or other valve allowing flow through the compression device 406b. The discharge side of the first compound separator recycle valve 419 is mechanically coupled to the compression device 406b and when the first compound separator recycle valve 419 is opened, flow is discharged into the compression device 406b. As the flow is conveyed through the compression device 406b that is driven by energy from the mechanical shaft/electrical cable 406a, the high pressure contained within the extraction flow discharge pipe 405 is transferred into the proportionately lower pressure flow within the first compound separator return discharge pipe 415. The discharge from the compression device 406b enters the extraction vessel return flow pipe 411 at increased pressure. The extraction vessel return flow pipe 411 is mechanically coupled to the compression device 406b and the extraction vessel 402 allowing for flow to return to the extraction vessel 402.

Generally, and dependent on relative densities, after the removal of the soluble compound, the insoluble solid or liquid compound may be removed from the SCF substantially contained within the extraction vessel 402, where the contents are discharged from the extraction vessel 402 into the extraction flow discharge pipe 405. The extraction flow discharge pipe 405 is mechanically coupled to the extraction vessel 402 at the inlet and the decompression device 406 at the outlet. The insoluble flow isolation valve 407 is mechanically coupled to the decompression device 406 at the inlet and the insoluble flow separation pipe 408 at the discharge. When the solid or liquid separation isolation valve 407 is opened, the mixed SCF insoluble solid or liquid compound and/or solid and liquid substrate exits the decompression device 406 and is conveyed through the insoluble flow separation pipe 408. When the insoluble flow separation pipe 408 is also coupled to the feed circulation valve 410, the valve remains closed and the flow is discharged into the second compound separator 420 that is mechanically coupled to the insoluble flow separation pipe 408. The second compound separator 420, for example, and without limitation, may comprise a hydro-cyclone, centrifuge, coalescer, another compound separator known in the art, or combination thereof. The second compound separator separates the SCF from the insoluble solid or liquid compound. The second compound separator 420 discharges the substantially pure SCF into the mechanically coupled second compound separator return discharge 421 pipe and the second compound separator 420 discharges the substantially pure second compound separator discharge 422 into the mechanically coupled Second compound separation vessel 404.

The insoluble solid or liquid compound may be stored in the second compound separation vessel 404 and/or removed from the process through the solid or liquid compound discharge 423 which is mechanically coupled to the second compound separation vessel 404. In one embodiment of the disclosure the pressure may be regulated if needed through the use of a second compound separation vessel pressure reduction vent 424 mechanically coupled to the second compound separation vessel 404. The substantially pure SCF with removed or reduced insoluble solid or liquid compound is conveyed from the second compound separator 420 through the second compound separator return discharge pipe 421 that is mechanically coupled to the second compound separator recycle valve 425. The discharge side of the second compound separator recycle valve 425 is mechanically coupled to the compression device 406b. When the second compound separator recycle valve 425 is opened, flow is discharged into the compression device 406b. As the flow is conveyed through the compression device 406b, the high pressure contained within the extraction flow discharge pipe 405 is transferred into the proportionately lower pressure flow contained within the second compound separator return discharge pipe 421 using methods well known in the art. The discharge from the compression device 406b enters the extraction vessel return flow pipe 411 at increased pressure. The extraction vessel return flow pipe 411 is mechanically coupled to the compression device 406b at the inlet and the extraction vessel 402 at the outlet allowing flow to return to the extraction vessel 402.

Figure 4B:
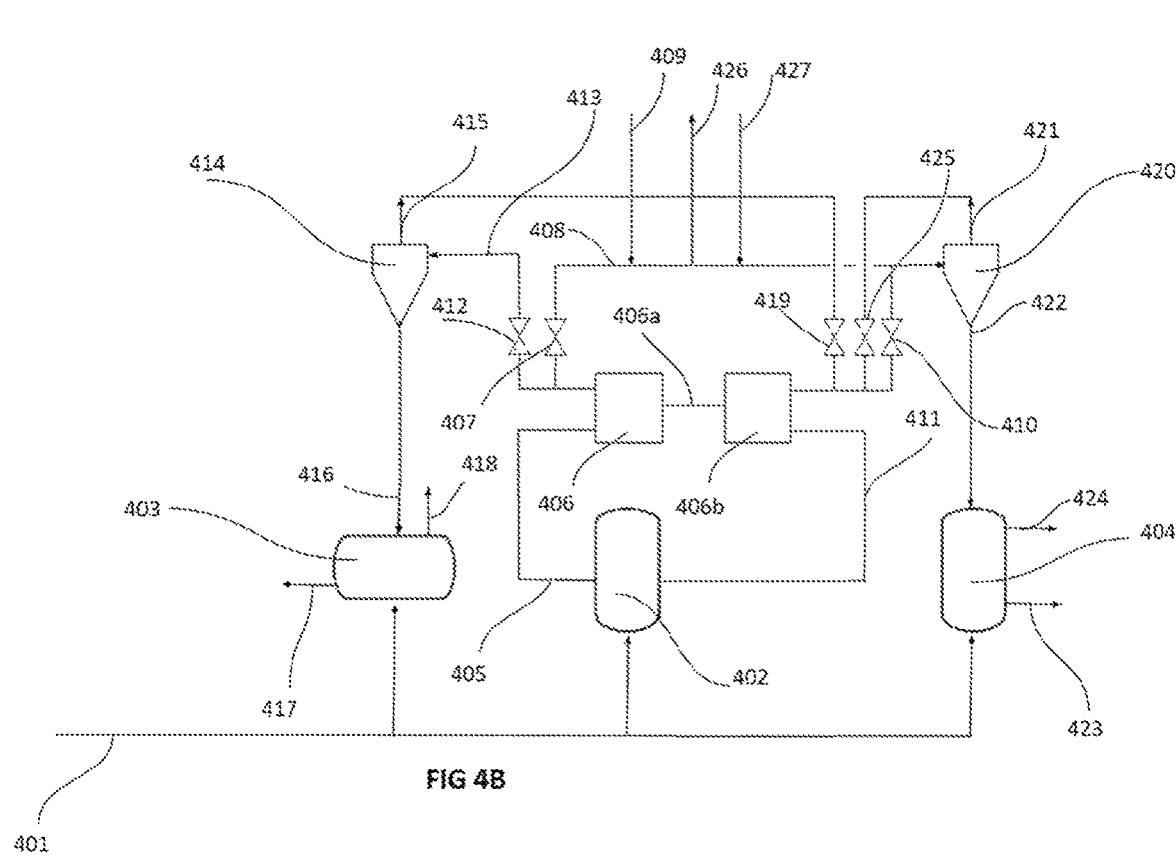

FIG. 4B describes another embodiment of the same disclosure whereby a cavitation system supply pipe 426 is mechanically coupled to the insoluble flow separation pipe 408 or other pipework or vessel (not shown). The flow substantially comprising SCF and a solid or liquid substrate and/or insoluble solid or liquid compound is conveyed through the cavitation system supply pipe 426 where it makes contact with a flow contraction (not shown). For example, and without limitation, the flow contraction (not shown) may be an orifice plate or venturi or other means that causes the pressure to be reduced in the flow below the SCF vapor pressure may be used. This reduction in pressure within the flow contraction (not shown) results in hydrodynamic cavitation that disrupts the solid or liquid substrate, thus increasing the rate of extraction. The flow is then discharged from the flow contraction (not shown) into a cavitation system return pipe 427 that is mechanically coupled to the flow contraction (not shown) and the insoluble flow separation pipe 408 or other pipework or vessel (not shown). The flow then discharges from the cavitation system return pipe 427 into the insoluble flow separation pipe 408 before being conveyed through the feed circulation valve 410. The subsequent steps described in previous embodiments are then followed. The cavitation system supply pipe 425 and cavitation system return pipe 426 may also be mechanically coupled to other sections of the system. For example, and without limitation, they may be coupled to the extraction vessel 402 or another vessel or pipe (not shown). Such embodiments utilizing interconnecting pipework (not shown) or vessels should be considered within the scope of this invention.

Figure 4C:
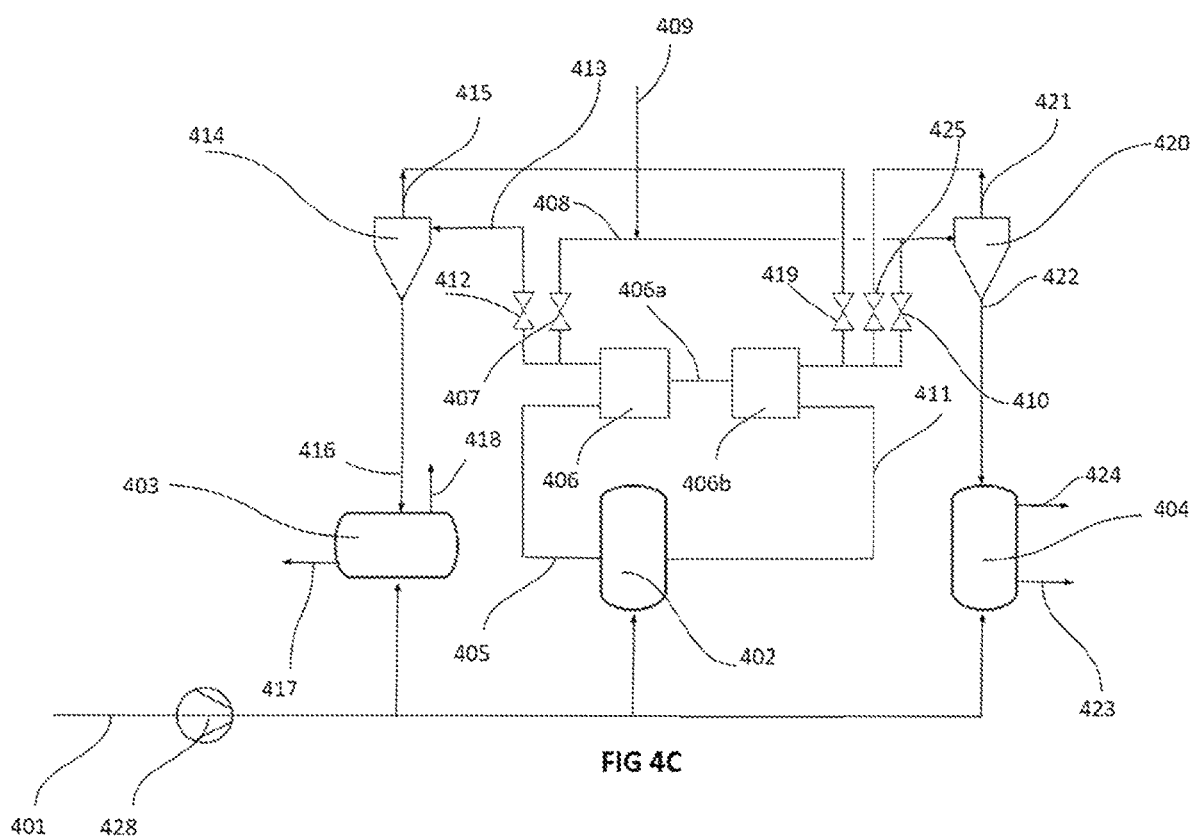

FIG. 4C describes another embodiment of the same disclosure where a SCF compression device 428 is mechanically coupled to the SCF stream 401 or plurality of SCF streams 401 at the inlet. The SCF compression device 428 discharge's into at least one of an extraction vessel 402, a first separation vessel 403, a second separation vessel 404, and other interconnecting pipework. The SCF compression device 428 allows for simultaneous or independent filling and pressurization of at least one of an extraction vessel 402, a first separation vessel 403, a second separation vessel 404, and other interconnecting pipework. The remainder of the steps within this embodiment of the same disclosure follow the steps described in previous embodiments.

It should be understood that the system shown in FIG. 1A-1E, FIG. 2A-2E FIG. 3A-3C and FIG. 4A-4C may be implemented in various arrangements, with a plurality of components. It should also be understood that where the terms flow, discharge, convey, conveying, draw, transport, or other means of transmitting gas, liquid, SCF, or solid components are used, the use of a pressure-retaining device, by way of example and not limitation, a pipe, a tube, a box-section, a casting, a forging or other means of retaining pressure between one component to another is also generally included and may be used in various configurations and arrangements. The term pipe is also a generic term used to describe a device that retains internal pressure while transporting substances between components. The term vessel is a generic term for an enclosed area that may be a vessel, a tank, a pipe, a tube, a receptacle, a chamber, a canister, a container, a flask, pipework or another enclosed area known in the art. In addition, the term flow can also be called extraction flow, insoluble flow or other used to describe the pipe or apparatus the specific flow or discharge is travelling through. The term valve can be interchanged with any means of segregating flow and/or different pressures within the system. The term mechanically coupled may also be described as operatively coupled refers to the connection between two components using welding, bolts, fasteners, casting, bonding, forging, or another joining method able to withhold pressure and external loads. The term operatively coupled may also be used to describe an electrical connection that provides a means of transferring power from one device or apparatus to another. The naming of a valve, pipe or other equipment is for exemplary purposes only and used to describe the different steps within the various embodiments of the disclosure, for example one named valve may provide a single function or plurality of functions detailed within the disclosure and does not represent that multiple separate valves must be used to perform each individual function.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. Incorporation by reference is limited such that no subject matter is incorporated that is contrary to the explicit disclosure herein, no claims included in the documents are incorporated by reference herein, and any definitions provided in the documents are not incorporated by reference herein unless expressly included herein.

The use of the word "a" or "an", when used in conjunction with the term "comprising" in the claims and/or the specification, may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step, or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature.

What is claimed is:

1. A method of extracting a soluble compound contained within at least one of an insoluble solid compound or an insoluble liquid compound using a supercritical fluid stream, the method comprises the following steps:
   a. providing an extraction vessel at least partially filled with a substrate comprising a soluble compound and at least one of the insoluble solid compound or the insoluble liquid compound;
   b. mixing the supercritical fluid stream with the substrate of step (a) to form an extraction flow;
   c. using a first compound separation vessel to decrease a pressure of the supercritical fluid stream to match the density thereof to that of at least one of the insoluble solid compound or an insoluble liquid compound, thereby causing separation of the soluble compound from the extraction flow within the first compound separator;
   d. directing at least one of the insoluble solid compound or an insoluble liquid compound and the supercritical fluid stream to the extraction vessel, while retaining the soluble compound in the first separation vessel;
   e. repeating steps (a) through (d) until all soluble compound is removed from the extraction flow;
   f. directing at least one of the insoluble solid compound or an insoluble liquid compound and the supercritical fluid stream to a second compound separator;
   g. decreasing the pressure of the supercritical fluid stream inside the second compound separation vessel, thereby causing a further reduction of the density of the supercritical fluid stream and separating thereof from at least one of the insoluble solid compound or an insoluble liquid compound within the second compound separator, and h. returning the supercritical fluid stream to the extraction vessel, while retaining at least one of the insoluble solid compound or an insoluble liquid compound inside the second compound separation vessel.

2. The method of claim 1, wherein the extraction vessel comprises an outlet with a solid compound screen configured to retain at least some of the insoluble solid compound inside thereof.

3. The method of claim 1, wherein step (a) further comprises a step of using a filter to separate at least some of the insoluble solid compound from the extraction flow and redirect the insoluble solid compound back to the extraction vessel.

4. The method of claim 1, wherein fluid pressure in the extraction vessel, the first compound separation vessel, or the second compound separation vessel is controlled using a compression device operatively connected thereto.

5. The method of claim 1, wherein a pressure of the extraction flow is controlled using a compression device operatively connected to a pipe carrying the extraction flow from the extraction vessel.

6. A method of extracting a soluble compound contained within at least one of an insoluble solid compound or an insoluble liquid compound using a supercritical fluid stream, the method comprises the following steps:
   a. providing an extraction vessel at least partially filled with a substrate comprising a soluble compound and at least one of the insoluble solid compound or the insoluble liquid compound;
   b. mixing the supercritical fluid stream with the substrate of step (a) to form an extraction flow;
   c. using a first compound separation vessel to decrease a pressure of the supercritical fluid stream to match the density thereof to at least one of the insoluble solid compound or an insoluble liquid compound, thereby causing separation of the soluble compound from the extraction flow;
   d. directing at least one of the insoluble solid compound or an insoluble liquid compound and the supercritical fluid stream to the extraction vessel, while retaining the soluble compound in the first separation vessel;
   e. repeating steps (a) through (d) until all soluble compound is removed from the extraction flow;
   f. directing at least one of the insoluble solid compound or an insoluble liquid compound and the supercritical fluid stream to a second compound separator;
   g. decreasing the pressure of the supercritical fluid stream inside the second compound separation vessel, thereby causing a further reduction of the density of the supercritical fluid stream and separating thereof from at least one of the insoluble solid compound or an insoluble liquid compound within the second compound separator, and
   h. returning the supercritical fluid stream to the extraction vessel, while retaining at least one of the insoluble solid compound or an insoluble liquid compound inside the second compound separation vessel.

7. The method of claim 6, wherein the extraction vessel comprises an outlet with a solid compound screen configured to retain at least some of the insoluble solid compound inside thereof.

8. The method of claim 6, wherein step (a) further comprises a step of using a filter to separate at least some of the insoluble solid compound from the extraction flow and redirect the insoluble solid compound back to the extraction vessel.

9. The method of claim 6, wherein fluid pressure in the extraction vessel, the first compound separation vessel, or the second compound separation vessel is controlled using a compression device operatively connected thereto.

10. The method of claim 6, wherein a pressure of the extraction flow is controlled using a compression device operatively connected to a pipe carrying the extraction flow from the extraction vessel.

11. A method of extracting a soluble compound contained within at least one of an insoluble solid compound or an insoluble liquid compound using a supercritical fluid stream, the method comprises the following steps:
   a. providing an extraction vessel at least partially filled with a substrate comprising a soluble compound and at least one of the insoluble solid compound or the insoluble liquid compound;
   b. mixing the supercritical fluid stream with the substrate of step (a) to form an extraction flow;
   c. operating a pressure exchanger positioned between the first compound separator and the extraction vessel, the pressure exchanger is configured to:
      i. transfer the extraction flow from the extraction vessel to the first compound separator where extraction vessel pressure is higher than the first compound separator pressure,
      ii. transfer first compound separator return discharge from the first compound separator to the extraction vessel where the first compound separator pressure is lower than the extraction vessel pressure,
      iii. transfer the extraction flow from the extraction vessel to the second compound separator where extraction vessel pressure is higher than the second compound separator pressure,
      iv. transfer second compound separator return discharge from the second compound separator to the extraction vessel,
   d. using the pressure exchanger to change a pressure of the supercritical fluid stream to match the density thereof to that of at least one of the insoluble solid compound or an insoluble liquid compound, thereby causing separation of the soluble compound from the extraction flow within the first compound separator;
   e. directing at least one of the insoluble solid compound or an insoluble liquid compound within the first compound separator return discharge from the first compound separator to the extraction vessel, while retaining the soluble compound in the first separation vessel;
   f. repeating steps (a) through (e) until all soluble compound is removed from the extraction flow;
   g. directing the SCF within the second compound separator return discharge from the second compound separator to the extraction vessel, while retaining the insoluble compound in the second separation vessel.

12. The method of claim 11, wherein a compression device is operatively coupled to at least one of the extraction vessel, the first compound separation vessel, or the second compound separation vessel.

13. The method of claim 11, wherein a valve is operatively coupled to at least an inlet or an outlet of the pressure exchanger to control flow therethrough.

14. The method of claim 11, wherein a cavitation-causing system is positioned downstream of the pressure exchanger.

15. The method as in claim 11, wherein the pressure exchanger comprises a decompression device and compression device, wherein operating the decompression device generates power used to energize the compression device.

16. The method of claim 15, wherein the compression device is operatively coupled to at least one of the extraction vessel, or the first compound separation vessel, or the second compound separation vessel.

17. A method of extracting a soluble compound contained within at least one of an insoluble solid compound or an insoluble liquid compound using a supercritical fluid stream, the method comprises the following steps:
   a. providing an extraction vessel at least partially filled with a substrate comprising a soluble compound and at least one of the insoluble solid compound or the insoluble liquid compound;
   b. mixing the supercritical fluid stream with the substrate of step (a) to form an extraction flow;
   c. operating a pressure exchanger positioned between the first compound separator and the extraction vessel, the pressure exchanger is configured to:
      i. transfer the extraction flow from the extraction vessel to the first compound separator where the extraction vessel pressure is higher than the first compound separator pressure,
      ii. transfer first compound separator return discharge from the first compound separator to the second compound separator where the first compound separator pressure is higher than the second compound separator pressure,
      iii. transfer second compound separator return discharge from the second compound separator to the extraction vessel where the second compound separator pressure is lower than the extraction vessel pressure,
   d. using the pressure exchanger to change a pressure of the supercritical fluid stream to match the density thereof to that of at least one of the insoluble solid compound or an insoluble liquid compound, thereby causing separation of the soluble compound from the extraction flow within the first compound separator;
   e. directing at least one of the insoluble solid compound or an insoluble liquid compound within the first compound separator return discharge from the first compound separator to the second compound separator, while retaining the soluble compound in the first separation vessel;
   f. repeating steps (a) through (e) until all soluble compound is removed from the extraction flow;
   g. directing the supercritical fluid within the second compound separator return discharge from the second compound separator to the extraction vessel, while retaining the insoluble compound in the second separation vessel.

18. The method of claim 17, wherein a compression device is operatively coupled to at least one of the extraction vessel, the first compound separation vessel, or the second compound separation vessel.

19. The method of claim 17, wherein a valve is operatively coupled to at least an inlet or an outlet of the pressure exchanger to control flow therethrough.

20. The method of claim 17, wherein a cavitation-causing system is positioned downstream of the pressure exchanger.

21. The method as in claim 17, wherein the pressure exchanger comprises a decompression device and compression device, wherein operating the decompression device generates power used to energize the compression device.

22. The method of claim 21, wherein the compression device is operatively coupled to at least one of the extraction vessel, or the first compound separation vessel, or the second compound separation vessel.

* * * * *